(12) United States Patent
Papenfuss

(10) Patent No.: US 9,517,076 B2
(45) Date of Patent: Dec. 13, 2016

(54) REAMING INSTRUMENT WITH ADJUSTABLE PROFILE

(71) Applicant: Lenkbar, LLC, Naples, FL (US)

(72) Inventor: Erik H. Papenfuss, Naples, FL (US)

(73) Assignee: Lenkbar, LLC, Naples, FL (US)

( * ) Notice: Subject to any disclaimer, the term of this patent is extended or adjusted under 35 U.S.C. 154(b) by 417 days.

(21) Appl. No.: 14/203,855

(22) Filed: Mar. 11, 2014

(65) Prior Publication Data

US 2015/0257769 A1    Sep. 17, 2015

(51) Int. Cl.
*A61B 17/00*    (2006.01)
*A61B 17/16*    (2006.01)

(52) U.S. Cl.
CPC ........ *A61B 17/1617* (2013.01); *A61B 17/1668* (2013.01); *A61B 17/1684* (2013.01)

(58) Field of Classification Search
None
See application file for complete search history.

(56) References Cited

U.S. PATENT DOCUMENTS

| | | |
|---|---|---|
| 1,082,553 A | 12/1913 | Pohlman |
| 2,649,001 A | 8/1953 | Fennell |
| 2,694,321 A | 11/1954 | Riza |
| 3,702,611 A | 11/1972 | Fishbein |
| 5,496,324 A | 3/1996 | Barnes |
| 5,591,170 A | 1/1997 | Spievack et al. |
| 6,283,971 B1 | 9/2001 | Temeles |
| 6,383,188 B2 | 5/2002 | Kuslich et al. |
| 6,726,690 B2 | 4/2004 | Eckman |
| 6,884,246 B1 | 4/2005 | Sonnabend et al. |
| 7,608,076 B2 | 10/2009 | Ezzedine |
| 7,722,615 B2 | 5/2010 | Botimer |
| 8,038,679 B2 | 10/2011 | Wieland |
| 8,241,289 B2 | 8/2012 | Maisonneuve |

(Continued)

FOREIGN PATENT DOCUMENTS

| | | |
|---|---|---|
| DE | 102010049456 A1 | 4/2012 |
| FR | 2886839 B1 | 7/2008 |

(Continued)

OTHER PUBLICATIONS

Entire patent prosecution history of U.S. Appl. No. 14/695,152, filed Apr. 24, 2015, entitled, "Reaming Instrument With Adjustable Profile."

(Continued)

*Primary Examiner* — Sameh Boles
(74) *Attorney, Agent, or Firm* — RatnerPrestia

(57) ABSTRACT

A reaming instrument, in accordance with one embodiment, includes a rotatable cutting head and a cutting face on a distal end of the cutting head. At least one radially displaceable cutting element has a cutting edge projecting in a distal direction from the cutting face. An adjustment element is operable to displace the cutting element toward a fully retracted state, or toward a fully expanded state. In another embodiment, a method of modifying a bone surface includes displacing at least one cutting element on a reamer instrument to a fully retracted state, inserting the instrument into a human or animal, operating an adjustment element to displace the cutting element toward an expanded state, and activating the cutting head to begin cutting the bone.

31 Claims, 7 Drawing Sheets

(56) References Cited

U.S. PATENT DOCUMENTS

| | | |
|---|---|---|
| 8,246,627 B2 | 8/2012 | Vanleeuwen et al. |
| 8,454,609 B2 | 6/2013 | Petit et al. |
| 8,480,673 B2 | 7/2013 | Yedlicka et al. |
| 8,480,675 B2 | 7/2013 | Betts |
| 8,523,867 B2 | 9/2013 | Rauscher et al. |
| 8,591,514 B2 | 11/2013 | Sherman |
| 8,632,546 B2 | 1/2014 | Sackett et al. |
| 2004/0073224 A1 | 4/2004 | Bauer |
| 2004/0092940 A1 | 5/2004 | Zwirnmann |
| 2005/0113836 A1 | 5/2005 | Lozier et al. |
| 2006/0217730 A1 | 9/2006 | Termanini |
| 2008/0114364 A1 | 5/2008 | Goldin et al. |
| 2008/0275449 A1* | 11/2008 | Sackett ............ A61B 17/1617 606/80 |
| 2011/0130760 A1 | 6/2011 | Anderson et al. |
| 2011/0251616 A1 | 10/2011 | Osman et al. |
| 2012/0209274 A1 | 8/2012 | Belaney et al. |
| 2013/0150859 A1 | 6/2013 | Kehres et al. |
| 2013/0165935 A1 | 6/2013 | Griffiths |

FOREIGN PATENT DOCUMENTS

| | | |
|---|---|---|
| WO | WO 2007/003243 A1 | 1/2007 |
| WO | WO 2012/125546 A1 | 9/2012 |
| WO | WO 2013/086340 A1 | 6/2013 |

OTHER PUBLICATIONS

International Search Report and Written Opinion for International Application No. PCT/US2015/17067 mailed May 27, 2015.
International Preliminary Report on Patentability and Written Opinion for International Application No. PCT/US2015/017067 issued Sep. 13, 2016, 11 pages.

* cited by examiner

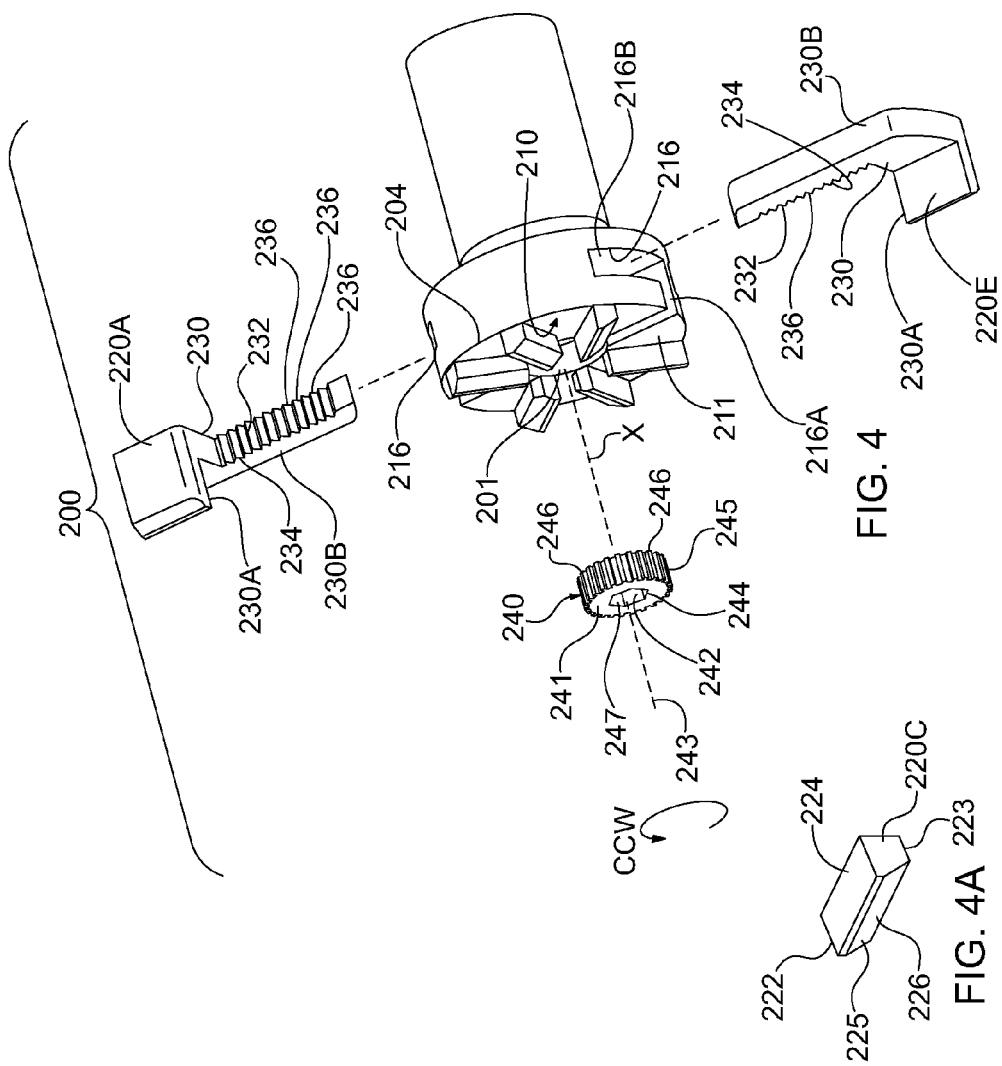

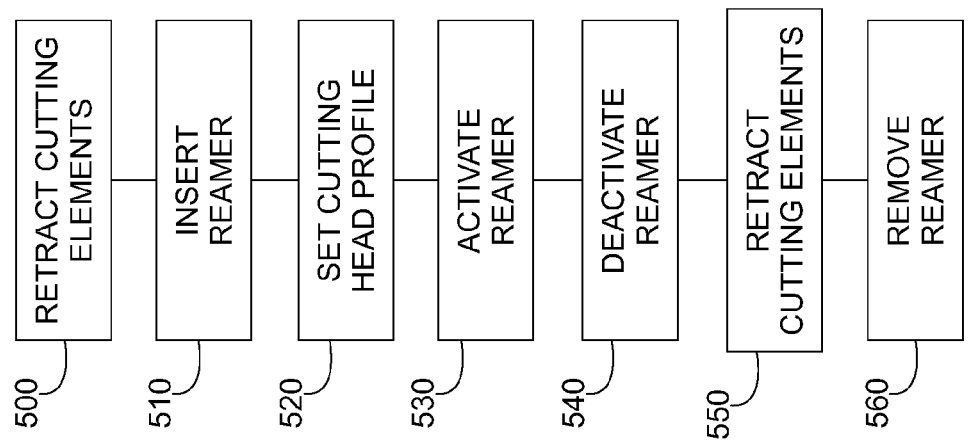
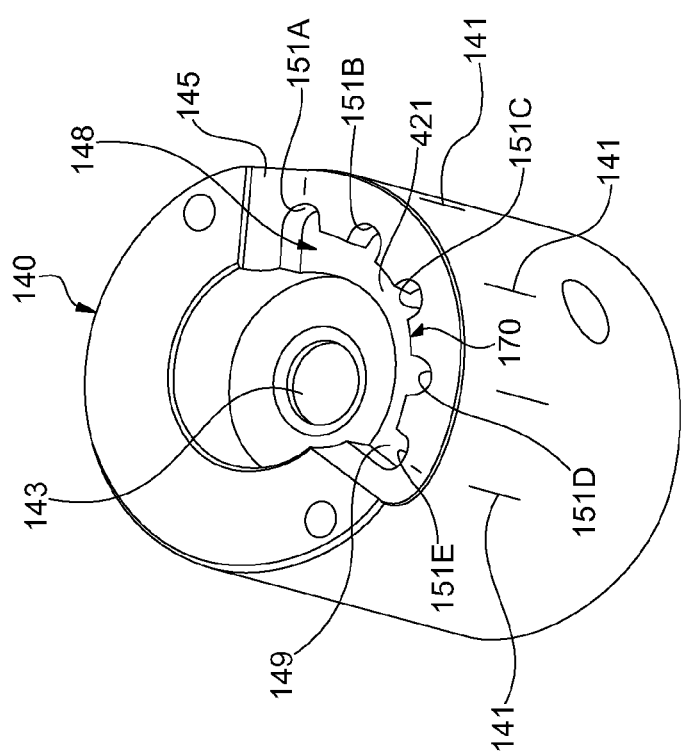

REAMING INSTRUMENT WITH ADJUSTABLE PROFILE

FIELD

The present invention relates generally to minimally invasive surgical instrumentation, and more particularly to a minimally invasive reaming instrument with an adjustment element that permits adjustment of the instrument's profile.

BACKGROUND

Joint arthroplasty procedures, sometimes referred to as "joint replacements", are commonly performed to relieve pain, restore mobility or address other issues caused by injury or degenerative conditions in a joint. Many types of arthroplasty procedures involve a partial or total replacement of the joint with prosthetic implants. In a total joint arthroplasty, the ends of the bones that are adjacent the joint to be replaced are cut away, or partially removed, to prepare and reshape the bone surface so that a prosthetic implant can be securely attached to the bone surface. This process of removing or reshaping the bone is often done with a tool referred to as a "reamer".

Certain joints, such as the glenohumeral joint (i.e. "shoulder joint"), are surrounded by bones and tissue, making it difficult to access the joint in a minimally invasive procedure. To access these joints with a reamer, the surgeon may have little choice but to make a large incision that accommodates the full profile size of the reamer. Large incisions can traumatize tissue, increase the risk of complications, and take a long time to fully heal.

SUMMARY

Applicants have developed reamers in accordance with the invention that feature an adjustable profile. The adjustable profile allows the profile of the reamers to be minimized, so that the reamers can be inserted through very small incisions and navigated through tissue in a minimally invasive manner.

In one beneficial aspect of the invention, a reaming instrument with an adjustable profile can include a rotatable cutting head having a proximal end, a distal end and an axis of rotation about which the cutting head is rotatable. A cutting face can be positioned on the distal end of the cutting head, the cutting face conforming to a plane extending generally perpendicular to the axis of rotation. At least one radially displaceable cutting element can have a cutting edge that projects in a distal direction from the cutting face. An adjustment element can be operably engaged with the at least one radially displaceable cutting element. The adjustment element can be operable in a first operation to displace the at least one radially displaceable cutting element radially inwardly with respect to the axis of rotation, and toward a fully retracted state in which the cutting head has a minimum cutting head profile. The adjustment element can also be operable in a second operation to displace the at least one radially displaceable cutting element radially outwardly with respect to the axis of rotation, and toward a fully expanded state in which the cutting head has a maximum cutting head profile.

In another beneficial aspect of the invention, the adjustment element can include a first engagement surface, and the at least one radially displaceable cutting element can include a second engagement surface.

In another beneficial aspect of the invention, the first engagement surface can be in direct contact with the second engagement surface.

In another beneficial aspect of the invention, the reaming instrument can have an adjustment element having a gear wheel with a first plurality of gear teeth.

In another beneficial aspect of the invention, the reaming instrument can have a gear wheel that defines a central bore having a bore axis.

In another beneficial aspect of the invention, the reaming instrument can have a gear wheel that defines a central bore, where the central bore is substantially parallel to and substantially coaxial with the axis of rotation of the cutting head.

In another beneficial aspect of the invention, the reaming instrument can have a gear wheel that defines a central bore that defines an inner wall, the inner wall having a hexagonal profile to form a hexagonal socket inside the gear wheel.

In another beneficial aspect of the invention, the reaming instrument can have at least one radially displaceable cutting element having a second plurality of gear teeth configured to mate with the first plurality of gear teeth on the gear wheel.

In another beneficial aspect of the invention, the reaming instrument can have at least one radially displaceable cutting element having a rack, the rack having a second plurality of gear teeth.

In another beneficial aspect of the invention, the reaming instrument can have at least one radially displaceable cutting element having an L-shaped body defining a first leg and a second leg extending in a direction generally perpendicular to the first leg.

In another beneficial aspect of the invention, the reaming instrument can have at least one radially displaceable cutting element having a rack, wherein the rack extends along a second leg of the cutting element.

In another beneficial aspect of the invention, the reaming instrument can have at least one radially displaceable cutting element having a cutting edge that projects from a first leg of the cutting element.

In another beneficial aspect of the invention, the reaming instrument can have a plurality of cutting elements projecting in the distal direction from the cutting face, with at least one radially displaceable cutting element being one of the plurality of cutting elements.

In another beneficial aspect of the invention, the reaming instrument can have a plurality of cutting elements that are uniformly spaced from one another on the cutting face.

In another beneficial aspect of the invention, the reaming instrument can have at least one radially displaceable cutting element with a cutting edge, at least a portion of the cutting edge projecting radially outwardly from a perimeter edge of the cutting face when the at least one radially displaceable cutting element is in a fully expanded state.

In another beneficial aspect of the invention, the reaming instrument can have at least one radially displaceable cutting element with a cutting edge, the cutting edge extending, in its entirety, inside a perimeter edge of the cutting face when the at least one radially displaceable cutting element is in a fully retracted state.

In another beneficial aspect of the invention, the reaming instrument can have a first radially displaceable cutting element having a first cutting edge, and a second radially displaceable cutting element having a second cutting edge. The first radially displaceable cutting element can be movable in a first radial direction toward the fully expanded state, and the second radially displaceable cutting element can be movable in a second radial direction toward the fully expanded state, the second radial direction being opposite the first radial direction. The reaming instrument can have a cutting face that is generally circular, with the second radially displaceable cutting element angularly offset from the first radially displaceable cutting element by an angle of approximately 180 degrees with respect to the generally circular cutting face. The first radially displaceable cutting element and the second radially displaceable cutting element can both be operably engaged with an adjustment element.

In another beneficial aspect of the invention, the reaming instrument can have a first radially displaceable cutting element having a first cutting edge, a second radially displaceable cutting element having a second cutting edge, a third radially displaceable cutting element having a third cutting edge, and a fourth radially displaceable cutting element having a fourth cutting edge. The third radially displaceable cutting element can be movable in a third radial direction toward a fully expanded state, and the fourth radially displaceable cutting element can be movable in a fourth radial direction toward the fully expanded state, the fourth radial direction being opposite the third radial direction. The first, second, third and fourth radially displaceable cutting elements can be angularly offset from one another by an angle of approximately 90 degrees. The third radially displaceable cutting element and the fourth radially displaceable cutting element can both be operably engaged with the adjustment element.

In another beneficial aspect of the invention, the reaming instrument can include a drill bit centrally located on the cutting face. In addition, the cutting face can define at least one slot that extends through the cutting face. A portion of at least one radially displaceable cutting element can extend within the at least one slot, with the at least one slot defining a path of travel for the radially displaceable cutting element as the radially displaceable cutting element is displaced between a fully expanded state and a fully retracted state.

In another beneficial aspect of the invention, the reaming instrument can include a drive shaft extending from the cutting head, the drive shaft operable to rotate the cutting head during a bone cutting procedure.

In another beneficial aspect of the invention, the reaming instrument can include an adjustment tool extending from an adjustment element, the adjustment tool configured to actuate the adjustment element in a first operation to displace at least one radially displaceable cutting element radially outwardly with respect to an axis of rotation, toward a fully expanded state, the adjustment tool also configured to actuate the adjustment element in a second operation to displace the at least one radially displaceable cutting element radially inwardly with respect to the axis of rotation, toward a fully retracted state.

In another beneficial aspect of the invention, the reaming instrument can include a drive shaft that defines a hollow passage in its interior, and wherein the adjustment tool extends through the hollow passage of the drive shaft. The adjustment tool can be rotatable independently of the drive shaft.

In another beneficial aspect of the invention, a method of modifying a surface of a bone in a human or animal includes selecting a reaming instrument having: (1) a rotatable cutting head comprising a proximal end, a distal end and an axis of rotation about which the cutting head is rotatable; (2) a cutting face positioned on the distal end of the cutting head, the cutting face conforming to a plane extending generally perpendicular to the axis of rotation; (3) at least one radially displaceable cutting element having a cutting edge, the cutting edge projecting in a distal direction from the cutting face; and (4) an adjustment element operably engaged with the at least one radially displaceable cutting element. The adjustment element can be operable in a first operation to displace the at least one radially displaceable cutting element radially inwardly with respect to the axis of rotation, and toward a fully retracted state in which the cutting head has a minimum cutting head profile. The adjustment element can also be operable in a second operation to displace the at least one radially displaceable cutting element radially outwardly with respect to the axis of rotation, and toward a fully expanded state in which the cutting head has a maximum cutting head profile.

In another beneficial aspect of the invention, the method of modifying a surface of a bone in a human or animal can include operating the adjustment element in a first operation to displace the at least one radially displaceable cutting element radially inwardly with respect to the axis of rotation, to the fully retracted state.

In another beneficial aspect of the invention, the method of modifying a surface of a bone in a human or animal can include inserting the reaming instrument into the human or animal.

In another beneficial aspect of the invention, the method of modifying a surface of a bone in a human or animal can include navigating the reaming instrument to a space around the surface of the bone.

In another beneficial aspect of the invention, the method of modifying a surface of a bone in a human or animal can include positioning the cutting face in a desired orientation and position to begin cutting the bone surface.

In another beneficial aspect of the invention, the method of modifying a surface of a bone in a human or animal can include operating the adjustment element in a second operation to displace the at least one radially displaceable cutting element radially outwardly with respect to the axis of rotation.

In another beneficial aspect of the invention, the method of modifying a surface of a bone in a human or animal can include activating the cutting head to begin cutting the bone.

In another beneficial aspect of the invention, the method of modifying a surface of a bone in a human or animal can include deactivating the cutting head to stop cutting the bone.

In another beneficial aspect of the invention, the method of modifying a surface of a bone in a human or animal can include operating the adjustment element in a first operation to displace the at least one radially displaceable cutting element radially inwardly with respect to the axis of rotation, to a fully retracted state.

In another beneficial aspect of the invention, the method of modifying a surface of a bone in a human or animal can include withdrawing the reaming instrument from the human or animal while maintaining the at least one radially displaceable cutting element in the fully retracted state.

BRIEF DESCRIPTION OF THE DRAWINGS

The summary and detailed description sections will be better appreciated when reviewed in conjunction with the drawing figures. The following drawing figures illustrate exemplary and non-limiting embodiments of the invention, and depict elements which can be combined and arranged either as shown, or in other combinations and arrangements that are contemplated by persons of skill in the art.

FIG. 4 is an enlarged exploded perspective view of components at one end of the reamer of FIG. 2;

FIG. 4A is an enlarged perspective view of one of the cutting elements at one end of the reamer of FIG. 2;

FIG. 8 is an enlarged perspective view of a component of the reamer of FIG. 2;

FIG. 9 is a block diagram describing one possible method of using a reamer in accordance with the invention;

DETAILED DESCRIPTION

Figure 1:
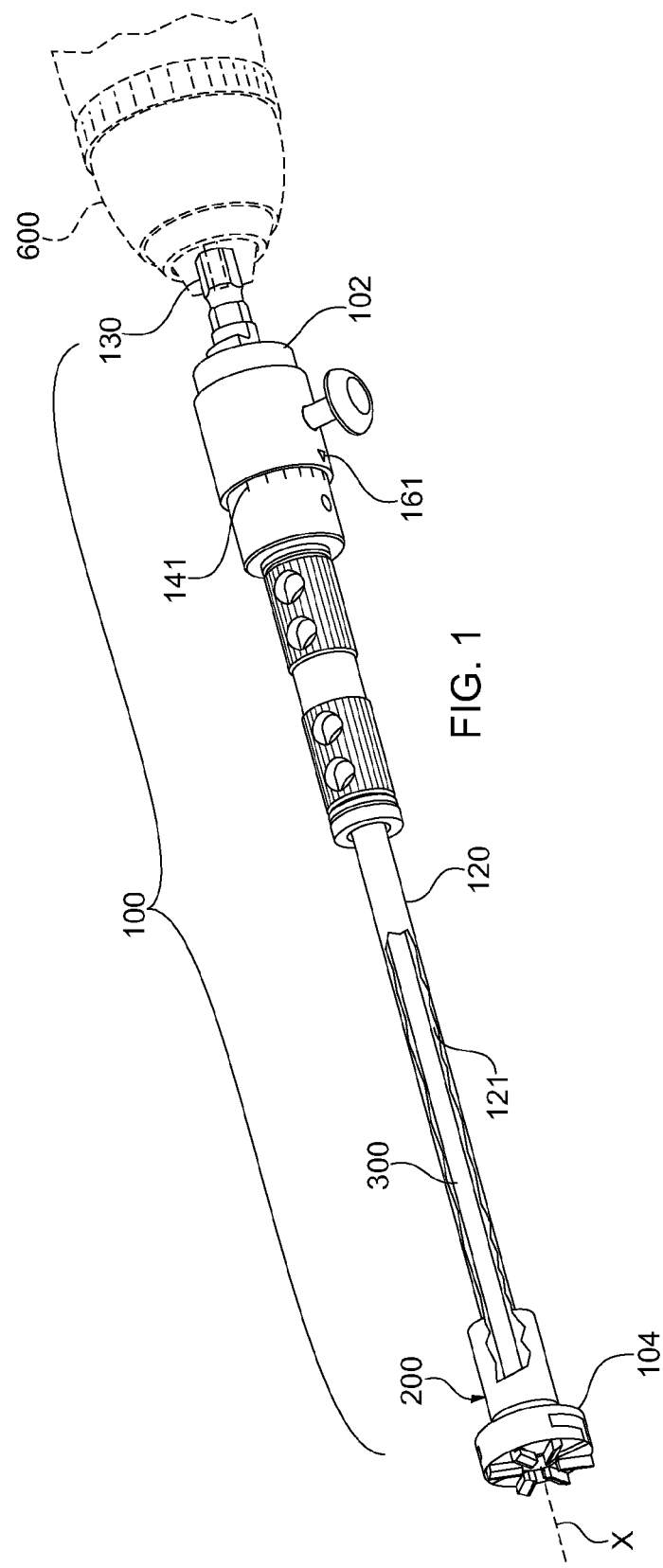
FIG. 1 is a perspective view of a reamer and power tool in accordance with one embodiment of the invention.

Although the invention is illustrated and described herein with reference to specific embodiments, the invention is not intended to be limited to the details shown. Rather, various modifications may be made in the details within the scope and range of equivalents of the claims and without departing from the invention.

Embodiments of the invention are described in this section in the context of how they could be used in a shoulder arthroplasty in humans, and more specifically in the preparation of bone surfaces on the glenoid portion of the scapula and the humerus. These descriptions are provided with the understanding that embodiments of the invention can also be used on other joints, and are not limited to shoulder arthroplasty procedures. For example, the disclosed embodiments, and other instruments in accordance with the invention, can be used for preparing bone surfaces in joints in human wrists, fingers, hips, knees, ankles, toes and the spine. Moreover, embodiments of the invention can be used for boring, reaming or planing bone surfaces, or other procedures for preparing bone surfaces. For simplicity, the following description will refer to embodiments of the invention as "reamers" regardless of how they are used.

Reamers in accordance with preferred embodiments of the invention allow for insertion of the reamer in a minimally invasive manner. This can be accomplished by utilizing an adjustable insertion "profile". The term "profile", as used herein, means the size of an object's footprint or shape, from an end view perspective. This definition of "profile" applies to any component or section of an instrument, but will be mainly used in this description in describing the cutting head of an instrument. When used in this manner, the profile of a cutting head means the footprint or shape of the cutting head from an end view of the cutting head. Profiles of cutting heads will be described in more detail in conjunction with embodiments described herein.

The profile of cutting heads in accordance with the invention can be adjustable in a variety of configurations. In general, the profile of instruments can be adjustable to at least two possible configurations: (1) a fully retracted or collapsed state, and (2) a fully expanded state. The term "fully retracted state" means a state in which the profile of the cutting head is minimized and occupies the least amount of lateral space. The term "fully expanded state" means a state in which the profile of the cutting head is maximized and occupies the greatest amount of lateral space. In some embodiments, the cutting head may also be adjustable to one or more partially expanded state(s). A "partially expanded state" means a state in which the profile of the cutting head is neither minimized nor maximized, with an adjustable portion of the cutting head positioned somewhere between the positions it would occupy in the fully retracted and fully expanded states. In a partially expanded state, that the cutting head's profile is larger than the profile the cutting head assumes in the fully retracted state, but smaller than the profile the cutting head assumes in the fully expanded state.

Figure 2:
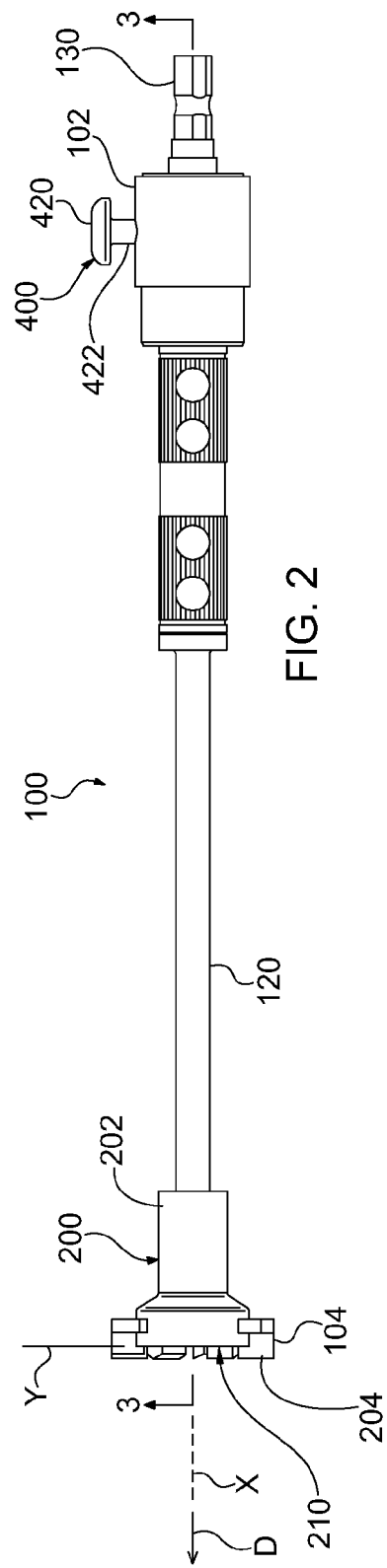
FIG. 2 is a side view of the reamer of FIG. 1.
Figure 3:
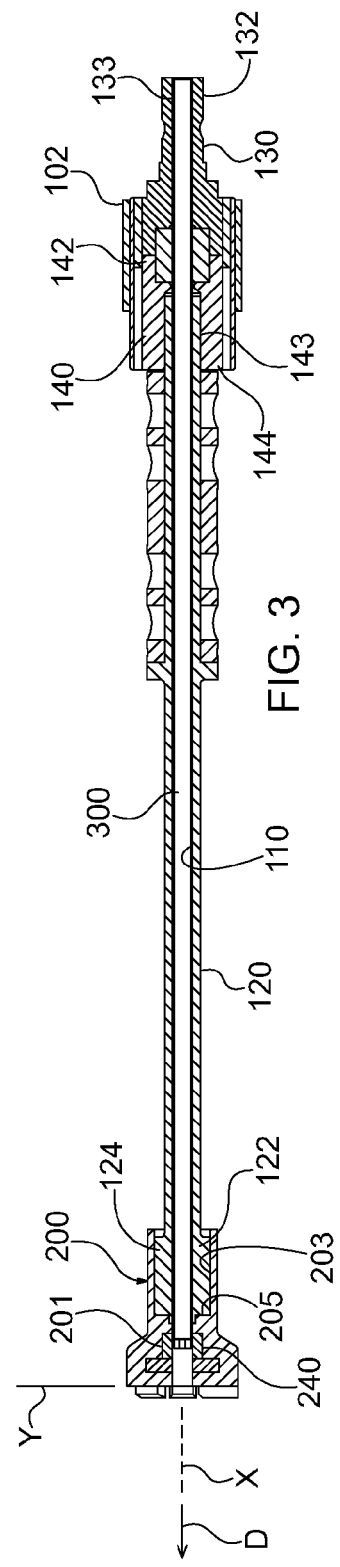
FIG. 3 is a cross section view of the reamer of FIG. 2.

Referring to FIGS. 1-3, a reamer 100 is shown in accordance with one possible embodiment of the invention. Reamer 100 has a proximal end 102, which can be directly handled or manipulated by a surgeon during a surgical procedure, and a distal end 104, which represents the end that is inserted into a patient. Proximal end 102 and distal end 104 are separated from one another by a hollow outer shaft, or "drive shaft" 120 that defines an interior space 121. Drive shaft 120 is connected to a rotatable cutting head 200 at distal end 104 of reamer 100.

Cutting head 200 has a proximal end 202 and a distal end 204 opposite the proximal end of the cutting head. Proximal end 202 of cutting head 200 connects with a distal end 122 of drive shaft 120. In particular, proximal end 202 of cutting head 200 defines a socket 203 having an internal geometry that receives a plug end 124 at distal end 122 of drive shaft 120. Socket 203 defines a rounded non-circular passage, and a rear wall 205. Inner shaft 300 is configured to be inserted into socket 203 with plug end 124 adjacent to or in proximity to rear wall 205. Plug end 124 is further configured to rotate in socket 203 and lock into a pair of apertures that extend through the wall of the socket. As will be described, the connection between cutting head 200 and drive shaft 120 allows the cutting head and drive shaft to rotate in unison when power is supplied to rotate the drive shaft. During rotation, cutting head 200 is rotatable about an axis of rotation "X".

Referring now to FIGS. 2-6, distal end 204 of cutting head 200 includes a cutting face 210. Cutting face 210 has a generally flat planar surface 211 that conforms to a cutting face plane "Y" shown in FIGS. 2 and 3. Cutting face plane Y extends generally perpendicular to axis of rotation X. As such, cutting face 210 is oriented to provide a cutting direction "D" generally parallel to axis of rotation X. Cutting face 210 has a perimeter edge 212 that conforms to a circle "C". Circle C has a center point "P" that intersects axis of rotation X.

Cutting heads in accordance with the invention can have one or more cutting elements arranged on the cutting face. The number of cutting elements on the cutting face, and the spatial arrangement of cutting elements on the cutting face, can depend on factors including but not limited to the type of procedure being performed and/or the particular bone surface being prepared.

Cutting head 200 includes a total of eight cutting elements 220A-220H that project from cutting face 210 in a distal direction. Each cutting element forms a raised section on cutting face 210. Cutting elements 220A-220H are arranged in a radial array on cutting face 210. That is, cutting elements 220A-220H appear in a circular pattern on cutting face 210 when the cutting face is viewed in the direction of axis of rotation X, shown in FIG. 5. In this arrangement, each of cutting elements 220A-220H is angularly offset from adjacent cutting elements about center point P by an angle of ⊖ as shown. The angular offset ⊖ between adjacent cutting elements is preferably the same, i.e. approximately 45 degrees, so that the cutting elements are uniformly spaced from one another. Each of cutting elements 220A-220H defines a cutting edge 221.

Referring to FIG. 4A, cutting elements 220A-220H each have an elongated cutting section 222 extending in a generally radial direction between center point P and perimeter edge 212. Each cutting section 222 has a first side 223, a second side 224 opposite the first side, and a third side 225 that interconnects the first side and second side. Second side 224 projects farther out in a distal direction from cutting face 210 than first side 223. As such, third side 225 defines a ramped surface 226 that gradually extends away from cutting face 210 as the ramped surface progresses in a counterclockwise direction CCW between the planes of the first side and second side, as shown.

Cutting head 200 has an adjustable profile that allows the cutting head to assume a fully retracted state, a fully expanded state and a partially expanded state. The profile of cutting head 200 is adjustable by virtue of cutting elements 220A and 220E, which are radially displaceable with respect to cutting face 210. That is, cutting elements 220A and 220E are displaceable toward or away from center point P of cutting face 210 and the axis of rotation X. The remaining cutting elements, i.e. 220B, 220C, 220D, 220F, 220G and 220H are fixed with respect to cutting face 210.

Figure 5:
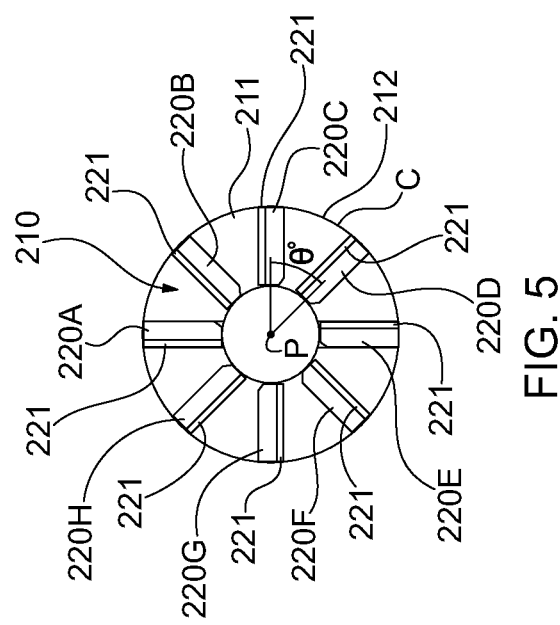
FIG. 5 is an end view of the reamer of FIG. 2, showing a minimized profile of the cutting head as it would appear in a fully retracted state.

Cutting elements 220A and 220E can be displaced radially inwardly with respect to the axis of rotation X, to the fully retracted state shown in FIG. 5. In this state, each of the cutting elements 220A and 220E and their respective cutting edges extend in their entirety inside perimeter edge 212 of cutting face 210, with the cutting face having a minimum cutting face profile. This profile produces a cut having the smallest diameter.

Figure 6:
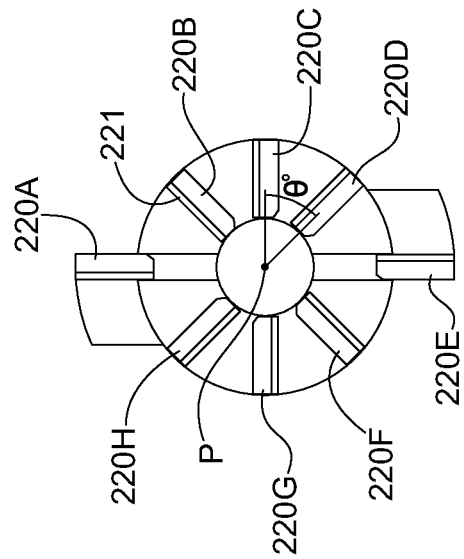
FIG. 6 is an end view of the reamer of FIG. 2, showing a maximized profile of the cutting head as it would appear in a fully expanded state.

Cutting elements 220A and 220E can also be displaced radially outwardly with respect to the axis of rotation X, to the fully expanded state shown in FIG. 6. In this state, at least a portion of cutting elements 220A and 220E and their respective cutting edges project radially outwardly from perimeter edge 212 of cutting face 210, with the cutting face having a maximum cutting face profile. This profile produces a cut having the largest diameter.

Cutting head 200 includes an adjustment element for adjusting the radial position of the radially displaceable cutting elements 220A and 220E. Adjustment elements in accordance with the invention can take various forms. For example, cutting head 200 includes an adjustment element in the form of a gear wheel 240 contained inside an interior space 201 inside cutting head 200. Gear wheel 240 has a ring shaped body 241 that defines a bore 242. Bore 242 has a central bore axis 243 that is substantially parallel to and substantially coaxial with axis of rotation X of cutting head 210. In addition, bore 242 defines an inner wall 247, the inner wall having a hexagonal profile that forms a hexagonal socket 244 inside the gear wheel. Ring shaped body 241 has a first engagement surface 245 defining a first plurality of gear teeth 246 that extend radially outwardly from the ring shaped body.

Gear wheel 240 operably engages cutting elements 220A and 220E to facilitate radial displacement of those cutting elements. Cutting elements 220A and 220E each have an L-shaped body 230 defining a first leg 230A and a second leg 230B extending in a direction generally perpendicular to the first leg. L-shaped bodies 230 are configured for insertion into similarly shaped L-shaped slots 216 in cutting head 200.

Each slot 216 adjoins interior space 201 inside cutting head 200 and defines two slot sections, a first slot section 216A and a second slot section 216B. Slot sections 216A are defined in and extend through cutting face 210, and slot sections 216B are defined in and extend through the outer circumference of cutting head 200.

Each first leg 230A includes a cutting section 222 and cutting edge 221 projecting outwardly from cutting face 210 when cutting head 200 is assembled. Each first leg 230A is configured to project through one of the first slot sections 216A, with its respective cutting section 222 projecting from cutting face 210. Cutting sections 222 associated with cutting elements 220A and 220E preferably project from cutting face 210 by the same distance that the fixed cutting elements 220B, 220C, 220D, 220F, 220G and 220H project from the cutting face.

Second legs 230B extend through slot sections 216B and into interior space 201. Each second leg 230B features a second engagement surface 232 in the form of a rack 234. Rack 234 includes a second plurality of gear teeth 236. The second plurality of gear teeth 236 directly contact and mate with the first plurality of gear teeth 246 on gear wheel 240. The engagement between the first plurality of gear teeth 246 on gear wheel 240, and the second plurality of gear teeth 236 on cutting elements 220A and 220E, facilitates radial adjustment of cutting elements 220A and 220E to change the cutting head profile to the fully retracted state, fully expanded state or a partially expanded state. By rotating gear wheel 240, rotational force is converted to linear force through the racks to expand and retract cutting elements 220A and 220E, and thereby adjust the cutting face profile.

Cutting element 220A is angularly offset from cutting element 220E by an angle of approximately 180 degrees with respect to circle C. In addition, cutting elements 220A and 220E are oriented with their second legs and cutting sections generally parallel to one another. In this arrangement, cutting element 220A is movable in a first radial direction toward the fully expanded state, and cutting element 220E is movable in a second radial direction toward the fully expanded state, the second radial direction being opposite the first radial direction.

Cutting elements 220A and 220E have identical configurations, and are mated with gear wheel 240 so that the gear wheel engages corresponding sections on each of the cutting elements at any one time. In this arrangement, the cutting edges of cutting elements 220A and 220E are equidistant from center point P of cutting face 210 at any time during adjustment of the cutting face profile.

Figure 7:
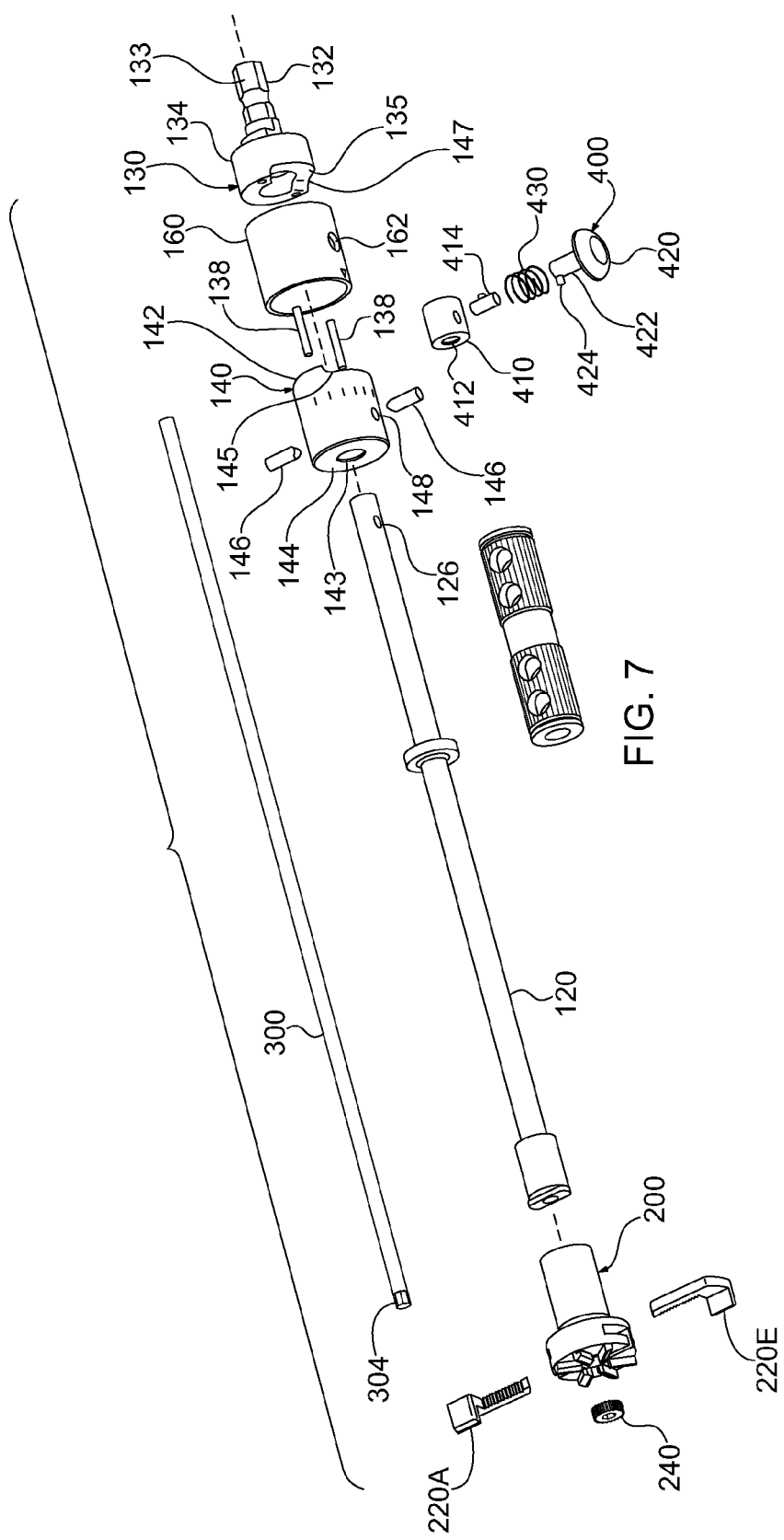
FIG. 7 is an exploded perspective view of the reamer of FIG. 2.

Adjustment elements in accordance with the invention can be coupled to, or permanently attached to, an adjustment tool. Referring to FIGS. 3 and 7, for example, gear wheel 240 is coupled to an adjustment tool having a hexagonal shaped inner shaft 300. Inner shaft 300 extends inside drive shaft 120 and into hexagonal socket 244 in gear wheel 240. A distal end 304 of inner shaft 300 has an exterior geometry that matches the geometry of inner wall 247 inside hexagonal socket 244. In this arrangement, gear wheel 240 is rotatable in response to rotation of inner shaft 300 when the inner shaft is inserted into hexagonal socket 244. Preferably, gear wheel 240 and inner shaft 300 share a common axis of rotation that is coaxial with axis of rotation X, as shown in the Figures.

Reamer 100 can ream bone surfaces when cutting head 200 is in the fully retracted state, or when the cutting head is in the fully expanded state, or when the cutting head is in a partially expanded state. As opposed to designs that fold back portions of the cutting face, or otherwise move sections of the cutting face out of the cutting face plane to reduce the profile of the cutting head, reamer 100 is designed so that all cutting edges on cutting face 210 remain in cutting face plane Y in all modes of operation. In particular, the cutting edges on cutting elements 220A and 220E remain in cutting face plane Y so that they are available for reaming bone in in the fully retracted state, the fully expanded state and any partially expanded state. This allows the profile of cutting head 200 to be reduced without sacrificing the reaming function of the cutting head when the profile is reduced. By keeping cutting elements 220A and 220E in cutting face plane Y in all states, the reamer offers a variable adjustable cutting face that provides a range of cutting face diameters.

Drive shaft 120 can be driven manually or by a driver tool such as a drill. Referring again to FIGS. 1-3 and 7, reamer 100 includes a drill attachment element 130 that allows a driver tool 600 to control rotation of drive shaft 120 and cutting head 200. Drill attachment element 130 has a proximal end 132 and a distal end 134. Proximal end 132 has a coupling element 133 that can be clamped into the chuck of a drill. Distal end 134 is connected with a barrel 140 by a pair of rods 138. Barrel 140 has a proximal end 142, a distal end 144 and a bore 143 extending between the proximal and distal ends of the barrel. Bore 143 receives drive shaft 120 in a fixed arrangement. A pair of diametrically opposed pins 146 extend through a first pair of diametrically opposed holes 148 in barrel 140, and a second pair of diametrically opposed holes 126 in drive shaft 120. Pins 146 lock drive shaft 120 and barrel 140 together so that the drive shaft and barrel are rotatable in unison.

Distal end 134 of drill attachment element 130 defines a cut section 135 that extends around approximately one half of the circumference of the distal end. Similarly, proximal end 142 of barrel 140 defines a cut section 145 that extends around approximately one half of the circumference of the proximal end. When drill attachment element 130 and barrel 140 are joined end to end, cut sections 135 and 145 align with one another to form a circumferential slot 147 that extends around approximately one half of the circumference of the drill attachment element and barrel.

The connection between drill attachment element 130 and barrel 140 is housed inside a ring shaped sleeve 160. Sleeve 160 overlaps the junction between drill attachment element 130 and barrel 140. A hole 162 extend through sleeve 160 and aligns with circumferential slot 147.

A number of different mechanisms can be employed in accordance with the invention to operate the cutting head generally, and more specifically to control the adjustment element during adjustment of the cutting head profile. Referring to FIGS. 2 and 7, reamer 100 includes an actuator assembly 400 located toward proximal end 102. Actuator assembly 400 includes a collar 410 that is fixed to inner shaft 300 inside sleeve 160. Collar 410 includes a bore 412 that receives inner shaft 300 in a fixed arrangement, and a stem 414 that extends in a radially outward direction. Stem 414 is positioned so that it aligns with and extends through circumferential slot 147. In addition, stem 414 extends through hole 162 in sleeve 160.

Actuator assembly 400 also includes a push button 420. Push button 420 has a cylindrical extension 422 that extends through hole 162 in sleeve 160, and through circumferential slot 147. A spring 430 is positioned over stem 414 and fits inside cylindrical extension 422 with the stem. A small tab 424 extends from cylindrical extension 422. Tab 424 is received in a groove 148 located in cut section 145 of barrel 140. Groove 148, which is shown best in FIG. 8, has a main section 149 and five side slots 151A-151E that extend radially outwardly from the main section.

Push button 420, sleeve 160, collar 410 and inner shaft 300 are rotatable in unison with respect to the axis of the inner shaft. In this arrangement, push button 420 can be rotated with respect to the axis of inner shaft 300 to rotate gear wheel 240 and adjust the position of cutting elements 220A and 220E. Spring 430 exerts a biasing force on push button 420 to bias the push button in a radially outward direction. This biasing force urges tab 424 to enter one of the side slots 151A-151E in groove 148. Each of side slots 151A-151E represents a stop position along groove 148 that prevents tab 424 from traveling along the groove. When tab 424 is captured in one of side slots 151A-151E, the position of push button 420 is locked relative to barrel 140, preventing rotation of gear wheel 240. Each of side slots 151A-151E thereby cooperates with tab 424 to form a locking mechanism 170 that locks and holds the position of cutting elements 220A and 220E in a desired position or setting, with each side slot corresponding to a different position or setting for cutting elements 220A and 220E.

Actuator assemblies in accordance with the invention can feature a variety of locking mechanisms that offer any number of settings. Locking mechanism 170 provides five settings, allowing cutting elements 220A and 220E to be locked in five different positions, or degrees of expansion, with respect to cutting face 210. Main section 419 of groove 418 forms a path of travel 421 for tab 424. Path of travel 421 spans an arc corresponding to an angle of 120 degrees. Side slots 151A-151E are incrementally spaced along path of travel 421. In this arrangement, each of side slots 151A-151E is angularly offset from an adjacent side slot by an angle of 30 degrees.

Side slot 151A corresponds to the fully retracted state, in which cutting elements 220A and 220E are not expanded at all with respect to cutting face 210. In this position, cutting head 200 has a cutting diameter of approximately 20 mm. Slot 151B corresponds to a first partially expanded state, in which cutting elements 220A and 220E are radially expanded with respect to cutting face 210, and in which cutting head 200 has a cutting diameter of approximately 23 mm. Slot 151C corresponds to a second partially expanded state, in which cutting elements 220A and 220E are radially expanded further with respect to cutting face 210, with cutting head 200 having a cutting diameter of approximately 26 mm. Slot 151D corresponds to a third partially expanded state, in which cutting elements 220A and 220E are radially expanded even further with respect to cutting face 210, with cutting head 200 having a cutting diameter of approximately 29 mm. Lastly, slot 151D corresponds to the fully expanded state, in which cutting head 200 has a cutting diameter of approximately 32 mm.

Referring again to FIG. 3, all of the components of reamer 100 define hollow passages that share a common longitudinal axis aligned with axis of rotation X. The hollow passages interconnect and collectively form a single through-passage 110. Through-passage 110 allows reamer 100 to be passed over a guide wire, guide pin or other means for guiding an instrument to a desired location in a patient.

Referring to FIG. 9, a method for using a reaming instrument in accordance with the invention is described in block diagram form. The block diagram in FIG. 9 depicts steps that could be performed in different sequences, and/or supplemented with other steps not represented in the Figure. Certain steps represented in FIG. 9 can also be repeated one or more times in a procedure. Therefore, the steps depicted in FIG. 9 are not intended to represent the only possible sequence of steps that is contemplated.

In step 500, the profile of the cutting head is minimized by moving the radially displaceable cutting elements radially inwardly. In this state, the profile of cutting the head is minimized so that a minimal incision is required to insert the cutting head through the patient's tissue and into proximity of the shoulder joint. This step can obviously be skipped if the cutting head is already adjusted to the fully retracted state.

In step 510, the reamer is inserted into the patient and advanced toward the shoulder joint while the cutting head is maintained in the fully retracted state. Once cutting head reaches a desired position to engage a bone surface, the profile of the cutting head is set in step 520. In setting the profile, the user can keep the radially displaceable cutting elements in the same position so that the cutting head has a minimum profile, or can adjust the radially displaceable cutting elements. Therefore, the term "set" as used herein in the context of the cutting head profile means keeping the position of the radially displaceable cutting elements in place without moving them, or adjusting the radially displaceable cutting elements to another position. If the user intends to adjust the radially displaceable cutting elements, the user can operate the adjustment tool to displace the radially displaceable cutting elements until the cutting head is in a partially expanded state or the fully expanded state.

Once the profile of the cutting head is set, the reamer is activated to rotate the cutting head and begin preparing the surface of the bone in step 530. One or more steps can be completed for preparing the bone surface, which may include shaving or otherwise removing bone material with one or more cutting head profiles used at a single location, or at multiple locations. Once the user is finished with the reaming instrument, the user deactivates the reamer in step 540. The user can then adjust the cutting head to the fully retracted state by retracting the adjustable cutting elements in step 550. Once the cutting head is in the fully retracted state, the user can remove the instrument from the patient in step 560.

A method of operating a reamer in accordance with the invention will now be described in more detail. To better visualize the steps, the method will refer to components of reamer instrument 100, with the understanding that the method could also describe the manner of operating other instrument configurations and arrangements in accordance with different embodiments of the invention.

A user, such as a surgeon or other party responsible for administering a surgical procedure, inserts inner shaft 300 through drive shaft 120 and into hexagonal socket 244 of gear wheel 240, so that the inner shaft is engaged with the gear wheel. Obviously, this step can be skipped or may not be applicable if inner shaft 300 is already attached to gear wheel 240. At this stage, push button 420 is positioned in a radially outward position under the bias of spring 430, so that tab 424 is engaged in one of side slots 151A-151E in a locked condition.

The actuator assembly 400 is utilized to minimize the profile of the cutting head 200 prior to inserting the reamer 100 into a patient. To minimize the profile of cutting head 200, the user can disengage the locking mechanism and move cutting elements 220A and 220E to the fully retracted state. To accomplish this, the user depresses push button 420, i.e. pushes the push button radially inwardly on the instrument, so that tab 424 is displaced out of the side slot and into main section 419 of groove 418. In this position, tab 424 is free to move along the path of travel 421, thereby allowing push button 420, collar 410, sleeve 160 and inner shaft 300 to rotate. While holding down push button 420 in the depressed position, the user rotates the push button in a first direction to rotate inner shaft 300. As inner shaft 300 rotates, the inner shaft rotates gear wheel 240. Gear wheel 240, in turn, displaces cutting elements 220A and 220E along slots 216. Cutting elements 220A and 220E are displaced radially inwardly toward center point P. Push button 420 is rotated in the first direction until tab 424 reaches one end of the path of travel 421, at which time, further rotation in the first direction is not possible. In this stopped condition, cutting head 200 is in the fully retracted state. The fully retracted state can be visually confirmed by observing the position of cutting elements 220A and 220E, which should be inside perimeter edge 212 of cutting face 210. The profile of cutting head 200 is therefore minimized so that the cutting head can fit through a minimal incision and be navigated through the patient's tissue into proximity of the shoulder joint, all in a minimally invasive manner.

Tab 424 is radially aligned with side slot 151A when cutting elements 220A and 220E reach the fully retracted state. Push button 420 can be released at this stage. Releasing push button 420 releases stored energy in spring 430 and pushes the push button and tab 424 radially outwardly. As push button moves radially outwardly, tab 424 enters side slot 151A, where it locks inner shaft 300, and cutting elements 220A and 220E in the fully retracted state. Gear wheel 240 preferably engages corresponding locations on racks 234 on cutting elements 220A and 220E, as noted earlier. Therefore, cutting elements 220A and 220E retract simultaneously and reach the fully retracted state at the same time.

Reamer 100 is inserted into the patient and advanced toward the shoulder joint while cutting head 200 is maintained in the fully retracted state. Once cutting head 200 reaches a desired position to engage a bone surface, reamer 100 can be activated to rotate cutting head 200 and begin preparing the surface of the bone, for example by shaving the bone surface. As such, cutting head 200 can be utilized to prepare the bone surface even when the cutting head is in the fully retracted state. Cutting head 200 makes the smallest diameter cut made when the cutting head is in the fully retracted state.

If a larger diameter cut is desired, locking mechanism 400 can be disengaged, and push button 420 rotated in a second direction opposite the first direction, to expand cutting elements 220A and 220E into one of the other four positions. For example, push button 420 can be rotated in the second direction relative to drive shaft 120 to rotate gear wheel 240 and expand cutting elements 220A and 220E radially outwardly to the first, second, or third partially expanded state. To accomplish this, push button 420 is depressed and rotated until tab 424 aligns with one of side slots 151B, 151C or 151D.

Alignment between tab 424 and side slots 151A-151E can be confirmed using markings or other indicia on the exterior of the instrument which indicate the relative positions of the tab and side slots. Alternatively, alignment can be confirmed by using tactile feedback, a combination of markings and tactile feedback, or other means. Sleeve 160 includes an arrow shaped marking 161 that can be rotated into alignment with one of five lines 141 on barrel 140. Arrow shaped marking 161 corresponds to the radial position of tab 424, and each of lines 141 corresponds to the radial position of one of side slots 151A-151E. Once tab 424 is aligned with one of side slots 151B, 151C or 151D, push button 420 is released, thereby releasing stored energy in spring 430.

Spring 430 returns push button 420 to the undepressed state and moves tab 424 into one of side slots 151B, 151C or 151D, locking cutting elements 220A and 220E in one of the partially expanded states.

If a maximum diameter cut is desired, inner shaft 300 can be rotated further in the second direction to rotate gear wheel 240 and expand cutting elements 220A and 220E radially outwardly to the fully expanded state. In this state, the diameter of any cut would be maximized. To accomplish this, push button 420 is depressed and rotated until tab 424 aligns with side slot 151E. Once tab 424 is aligned with side slot 151E, push button 420 is released. Spring 430 returns push button 420 to the undepressed state and moves tab 424 into side slot 151E, locking cutting elements 220A and 220E in the fully expanded state.

Depending on the type of procedure, reamer 100 can be used to make a series of cuts of different sizes, all in the same location, or in different locations, while the reamer is inserted into the shoulder joint. For example, reamer 100 can be operated with cutting head 200 in the fully expanded state to produce a shallow cut having a relatively large diameter. Then, without moving reamer 100 from the location of the cut, the profile of cutting head 200 can be reduced by rotating inner shaft 300 in the second direction to retract cutting elements 220A and 220E. Once cutting elements 220A and 220E are retracted to the desired positions, cutting can be resumed to produce a deeper section with a smaller diameter. This combination of cuts, or other combinations, can be performed to produce complex surface preparations that feature different diameters at different depths within the bone.

Once the bone surface is prepared at a specific location, reamer 100 can either be moved to a different location to prepare another bone surface, or be removed from the patient. In either case, the user can reduce the profile of cutting head 200 to the fully retracted state, prior to moving the cutting head. Cutting head 200 occupies the smallest profile in the fully retracted state, so that minimal contact or interference with surrounding bone or tissue occurs while the cutting head is navigated to other bone surfaces, or while reamer 100 is withdrawn from the patient.

Figures 10, 11:
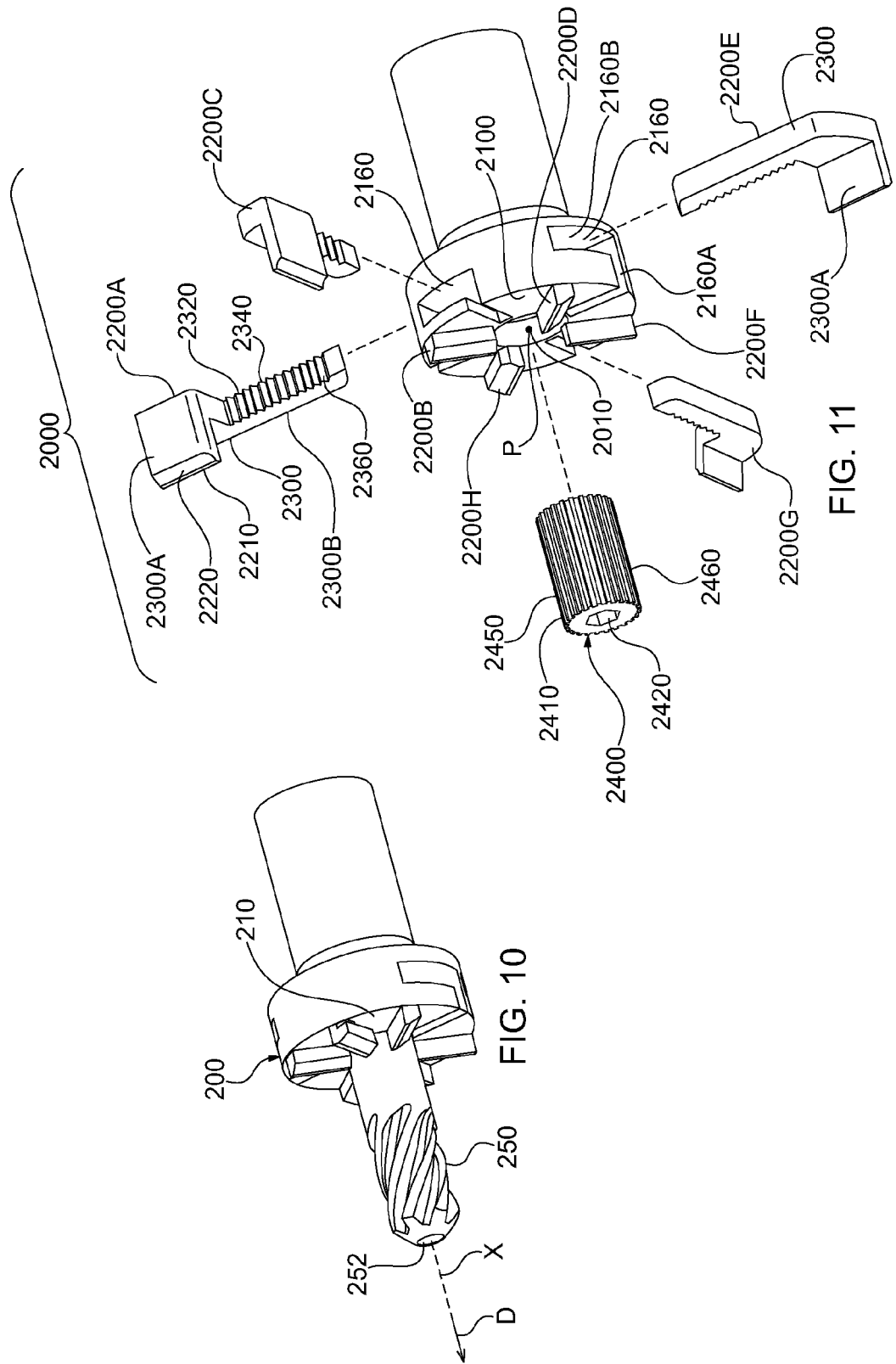
FIG. 10 is an enlarged perspective view of components at one end of the reamer of FIG. 2, with an optional drill bit attached to the cutting head of the reamer.
FIG. 11 is an enlarged exploded perspective view of components of a reamer in accordance with an alternative embodiment.

Referring now to FIG. 10, cutting head 200 is shown with an optional drill bit 250 attached to cutting face 210. Drill bit 250 can be used a centering guide to stabilize and control cutting head 200 as the cutting face 210 advances into a bone surface. For example, drill bit 250 can be driven into a pilot hole to guide cutting head 200 so that the cutting head remains stable and follows the desired cutting path. Drill bit 250 is cannulated, i.e. the drill bit defines a hollow central passage 252 like inner shaft 300, gear wheel 240 and other components of reamer 100 to allow the drill bit and the rest of the assembly to be advanced over a guide wire, guide pin or other guide means.

Thus far, examples have been described and illustrated that feature two radially displaceable cutting elements. Reamers in accordance with the invention need not feature two radially displaceable cutting elements, as other reamers having fewer or more displaceable cutting elements are also contemplated to be within the scope of the invention. For example, reamers in accordance with the invention can feature a cutting head with only one radially displaceable cutting element. One example could have the same identical arrangement as reamer 100, but instead of having two displaceable cutting elements 220A and 220E and two slots 216 in cutting head, the cutting head would have only one displaceable cutting element, e.g. the cutting element corresponding with cutting element 220A, and one slot. The cutting element corresponding to cutting element 220E would appear identical to any of the fixed cutting elements 220B, 220C, 220D, 220F, 220G or 220H, and the one of the slots 216 would not be present in the cutting head.

Reamers in accordance with the invention can also feature a cutting head with more than two radially displaceable cutting elements. Referring now to FIG. 11, a cutting head 2000 having four radially displaceable cutting elements is shown. In particular, cutting head 2000 includes four radially displaceable cutting elements 2200A, 2200C, 2200E and 2200G, and four fixed cutting elements 2200B, 2200D, 2200F and 2200H, uniformly arranged on a cutting face 2100. Many of the features of cutting head 2000 are similar, if not identical, to features of cutting head 200.

Each of the radially displaceable cutting elements 2200A, 2200C, 2200E and 2200G has an L-shaped body 2300 defining a first leg 2300A and a second leg 2300B extending in a direction generally perpendicular to the first leg. L-shaped bodies 2300 are configured for insertion into similarly shaped L-shaped slots 2160 in cutting head 2000. Each slot 2160 adjoins an interior space 2010 inside cutting head 2000 and defines two slot sections, a first slot section 2160A and a second slot section 2160B. Each slot section 2160A is defined in and extends through cutting face 2100, and each slot section 2160B is defined in and extends through the outer circumference of cutting head 2000.

Each first leg 2300A includes a cutting section 2220 and cutting edge 2210 projecting outwardly from cutting face 2100. Cutting head 2000 also includes an adjustment element in the form of a gear wheel 2400 housed in interior space 2010. Gear wheel 2400 has a cylindrical shaped body 2410 with an axial length that is slightly longer than gear wheel 240. Body 2410 defines a bore 2420 and features a first engagement surface 2450. First engagement surface 2450 defines a first plurality of gear teeth 2460 that extend radially outwardly from body 2410.

Second legs 2300B of radially displaceable cutting elements 2200A, 2200C, 2200E and 2200G extend through slot sections 2160B and into interior space 2010. Each second leg 2300B features a second engagement surface 2320 in the form of a rack 2340. Rack 2340 includes a second plurality of gear teeth 2360. The second plurality of gear teeth 2360 directly contact and mate with the first plurality of gear teeth 2460 on gear wheel 2400. The engagement between the first plurality of gear teeth 2460 and second plurality of gear teeth 2360 facilitates radial adjustment of cutting elements 2200A, 2200C, 2200E and 2200G to adjust the cutting head profile to the fully retracted state, fully expanded state or a partially expanded state.

Cutting elements 2200A, 2200C, 2200E and 2200G are angularly offset from one another by an angle of approximately 90 degrees with respect to a center point P. First legs 2300A associated with cutting elements 2200C and 2200G are slightly longer that the first legs associated with cutting elements 2200A and 2200E, but all cutting edges 2210 project from cutting face 2100 by the same distance. In this arrangement, second legs 2300B associated with cutting elements 2200C and 2200G are positioned proximally with respect to the second legs associated with cutting elements 2200A and 2200E, so that the paths of displacement of cutting elements 2200A and 2200E do not intersect and obstruct the paths of displacement of cutting elements 2200C and 2200G.

While preferred embodiments of the invention have been shown and described herein, it will be understood that such embodiments are provided by way of example only. Numerous variations, changes and substitutions will occur to those skilled in the art without departing from the scope of the invention.

For example, drive shaft 120, cutting head 200 and inner shaft 300 are shown and described in the drawing figures with substantially rigid tubular bodies. Drive shafts, cutting heads and inner shafts in accordance with the invention may also incorporate one or more flexible sections made up of interlocking sections that allow the components to rotate and flex, as described in U.S. Pat. No. 8,366,559 by the same inventors, the content of which is incorporated by reference herein in its entirety. For example, drive shafts, cutting heads, inner shafts and other components in accordance with the invention can be constructed with Applicants' flexible shaft being sold or licensed under the trademark FLEXMETRIC™.

In addition, cutting heads in accordance in the invention need not have the same number, arrangement and/or type of cutting elements described and illustrated in the drawing figures. For example, cutting heads in accordance with the invention can include as few as one cutting element, and as many as 10, 12, 14 or more cutting elements. The cutting elements need not be uniformly spaced from one another in a radial array, but can be randomly dispersed on a cutting face.

Moreover, reamers in accordance with the invention can have any number of settings or positions for the radially displaceable cutting elements. For example, radially displaceable cutting elements in accordance with the invention can be set to three positions: a fully retracted position, a fully expanded position, and one partially expanded position in between the fully retracted position and fully expanded position. Embodiments that use grooves and side slots to adjust the setting, the groove would feature three side slots, with each side slot corresponding to one of the settings. This embodiment would feature a barrel similar to barrel 140, but having a groove with only three side slots corresponding to side slots 151A, 151C and 151E, for example. It will be understood to those skilled in the art that other embodiments can feature more side slot, so as to offer more settings, and smaller incremental adjustments. For example, a reamer in accordance with the invention may feature a barrel with 7 side slots along an arc-shaped groove, each side slot being angularly offset by an angle of 20 degrees. The amount of incremental adjustment can be controlled as a function of each angular offset, relative tab size, relative side slot size and other variables. The total range of adjustment can be controlled as a function of arc length, which may be lesser or greater than 120 degrees.

Furthermore, components of reamers in accordance with the invention can have relative dimensions, shapes and configurations that deviate significantly from components shown in the drawing figures. For example, socket 203 on cutting head 200 is shown with a relatively long axial length in comparison to the axial length of the cutting elements. Although the drawings are not necessarily to scale, socket 203 can be much shorter than the length shown in the drawing figures, and still be able to connect with drive shaft 120. A shorter axial length reduces the overall size and mass of the reamer, and therefore be desirable in certain applications In addition, plug end 124 may have a different geometry and mechanism for coupling with socket 203. For example, plug end 124 may have one or more detents on the side of the plug end that cooperate with slots inside socket 203 in a bayonet-type connection. In the bayonet-type connection, the plug end can be coupled to the cutting head by inserting the plug end in the socket, with the detents in the slots, and then twisting the plug end to lock the plug end in the socket.

Accordingly, it is intended that the appended claims cover all such variations as fall within the spirit and scope of the invention.

What is claimed:

1. A reaming instrument with an adjustable profile, the reaming instrument comprising:
    a rotatable cutting head comprising a proximal end, a distal end and an axis of rotation about which the cutting head is rotatable;
    a cutting face positioned on the distal end of the cutting head, the cutting face conforming to a plane extending generally perpendicular to the axis of rotation;
    at least one radially displaceable cutting element having a cutting edge, the cutting edge projecting in a distal direction from the cutting face; and
    an adjustment element operably engaged with the at least one radially displaceable cutting element,
    the adjustment element being operable in a first operation to displace the at least one radially displaceable cutting element radially inwardly with respect to the axis of rotation, and toward a fully retracted state in which the cutting head has a minimum cutting head profile, the adjustment element also being operable in a second operation to displace the at least one radially displaceable cutting element radially outwardly with respect to the axis of rotation, and toward a fully expanded state in which the cutting head has a maximum cutting head profile.

2. The reaming instrument of claim 1, wherein the adjustment element comprises a first engagement surface, and the at least one radially displaceable cutting element comprises a second engagement surface.

3. The reaming instrument of claim 2, wherein the first engagement surface is in direct contact with the second engagement surface.

4. The reaming instrument of claim 1, wherein the adjustment element comprises a gear wheel having a first plurality of gear teeth.

5. The reaming instrument of claim 4, wherein the gear wheel defines a central bore having a bore axis.

6. The reaming instrument of claim 5, wherein the central bore is substantially parallel to and substantially coaxial with the axis of rotation of the cutting head.

7. The reaming instrument of claim 5, wherein the central bore defines an inner wall, the inner wall having a hexagonal profile to form a hexagonal socket inside the gear wheel.

8. The reaming instrument of claim 5, wherein the at least one radially displaceable cutting element comprises a second plurality of gear teeth configured to mate with the first plurality of gear teeth on the gear wheel.

9. The reaming instrument of claim 8, wherein the at least one radially displaceable cutting element comprises a rack, and the rack comprises the second plurality of gear teeth.

10. The reaming instrument of claim 9, wherein the at least one radially displaceable cutting element has an L-shaped body defining a first leg and a second leg extending in a direction generally perpendicular to the first leg.

11. The reaming instrument of claim 10, wherein the rack extends along the second leg.

12. The reaming instrument of claim 10, wherein the cutting edge of the at least one radially displaceable cutting element projects from the first leg.

13. The reaming instrument of claim 1, wherein the cutting face comprises a plurality of cutting elements projecting in the distal direction from the cutting face, the at least one radially displaceable cutting element being one of the plurality of cutting elements.

14. The reaming instrument of claim 13, wherein the plurality of cutting elements are uniformly spaced from one another on the cutting face.

15. The reaming instrument of claim 1, wherein at least a portion of the cutting edge of the at least one radially displaceable cutting element projects radially outwardly from a perimeter edge of the cutting face when the at least one radially displaceable cutting element is in the fully expanded state.

16. The reaming instrument of claim 1, wherein the cutting edge of the at least one radially displaceable cutting element extends, in its entirety, inside a perimeter edge of the cutting face when the at least one radially displaceable cutting element is in the fully retracted state.

17. The reaming instrument of claim 1, wherein the at least one radially displaceable cutting element comprises a first radially displaceable cutting element having a first cutting edge, and a second radially displaceable cutting element having a second cutting edge.

18. The reaming instrument of claim 17, wherein the first radially displaceable cutting element is movable in a first radial direction toward the fully expanded state, and the second radially displaceable cutting element is movable in a second radial direction toward the fully expanded state, the second radial direction being opposite the first radial direction.

19. The reaming instrument of claim 17, wherein the cutting face is generally circular, and the second radially displaceable cutting element is angularly offset from the first radially displaceable cutting element by an angle of approximately 180 degrees with respect to the generally circular cutting face.

20. The reaming instrument of claim 17, wherein the first radially displaceable cutting element and the second radially displaceable cutting element are both operably engaged with the adjustment element.

21. The reaming instrument of claim 17, wherein the at least one radially displaceable cutting element further comprises a third radially displaceable cutting element having a third cutting edge, and a fourth radially displaceable cutting element having a fourth cutting edge.

22. The reaming instrument of claim 21, wherein the third radially displaceable cutting element is movable in a third radial direction toward the fully expanded state, and the fourth radially displaceable cutting element is movable in a fourth radial direction toward the fully expanded state, the fourth radial direction being opposite the third radial direction.

23. The reaming instrument of claim 21, wherein the first, second, third and fourth radially displaceable cutting elements are angularly offset from one another by an angle of approximately 90 degrees.

24. The reaming instrument of claim 21, wherein the third radially displaceable cutting element and the fourth radially displaceable cutting element are both operably engaged with the adjustment element.

25. The reaming instrument of claim 1, wherein the cutting face comprises a drill bit centrally located on the cutting face.

26. The reaming instrument of claim 1, wherein the cutting face defines at least one slot that extends through the cutting face.

27. The reaming instrument of claim 26, wherein a portion of the at least one radially displaceable cutting element extends within the at least one slot, the at least one slot defining a path of travel for the at least one radially displaceable cutting element as the at least one radially displaceable cutting element is displaced between the fully expanded state and the fully retracted state.

28. The reaming instrument of claim 1 comprising a drive shaft extending from the cutting head, the drive shaft operable to rotate the cutting head during a bone cutting procedure.

29. The reaming instrument of claim 28 comprising an adjustment tool extending from the adjustment element, the adjustment tool configured to actuate the adjustment element in the first operation to displace the at least one radially displaceable cutting element radially outwardly with respect to the axis of rotation, toward the fully expanded state, the adjustment tool also configured to actuate the adjustment element in the second operation to displace the at least one radially displaceable cutting element radially inwardly with respect to the axis of rotation, toward the fully retracted state.

30. The reaming instrument of claim 29, wherein the drive shaft defines a hollow passage in its interior, and wherein the adjustment tool extends through the hollow passage of the drive shaft.

31. The reaming instrument of claim 30, wherein the adjustment tool is rotatable independently of the drive shaft.

* * * * *